United States Patent [19]

Bielefeldt et al.

[11] Patent Number: 5,530,169
[45] Date of Patent: Jun. 25, 1996

[54] PROCESS FOR THE PREPARATION OF SATURATED, FLUORINE-CONTAINING AND CHLORINE-FREE HYDROCARBONS

[75] Inventors: Dietmar Bielefeldt, Ratingen; Rudolf Braden, Odenthal; Michael Negele, Cologne; Heinz Ziemann, Leichlingen, all of Germany

[73] Assignee: Bayer Aktiengesellschaft, Leverkusen, Germany

[21] Appl. No.: 326,143

[22] Filed: Oct. 19, 1994

Related U.S. Application Data

[63] Continuation of Ser. No. 759,793, Sep. 13, 1991, abandoned, which is a continuation of Ser. No. 651,846, Feb. 4, 1991, abandoned.

[30] Foreign Application Priority Data

Feb. 14, 1990 [DE]  Germany .......................... 40 04 494.7

[51] Int. Cl.$^6$ ................................... C07C 19/08
[52] U.S. Cl. ............................ 570/175; 570/176
[58] Field of Search ...................... 570/175, 176

[56] References Cited

U.S. PATENT DOCUMENTS 4,873,381  10/1989  Kellner et al. .
4,902,839   2/1990  Bielefeldt et al. ...................... 570/175

FOREIGN PATENT DOCUMENTS 3735467  10/1987  Germany .............................. 570/175
3735467   5/1989  Germany .
3818692   7/1989  Germany .

OTHER PUBLICATIONS

Chemical Abstracts, vol. 101, No. 7, Aug. 13, 1984, Columbus, Ohio, USA Y. Huang et al. "Palldium–polyfluororalkenes and–alkynes" p. 572, Col. 1, para. No. 54 508u & Youji Huaxue 1984, (2), 125–8.

*Primary Examiner*—Alan Siegel
*Attorney, Agent, or Firm*—William C. Gerstenzang; Sprung Horn Kramer & Woods

[57] ABSTRACT

Saturated, fluorine-containing and chlorine-free hydrocarbons are prepared by catalytically hydrogenating unsaturated, fluorine- and chlorine-containing hydrocarbons at temperatures above 80° C. in the gas phase.

6 Claims, No Drawings

PROCESS FOR THE PREPARATION OF SATURATED, FLUORINE-CONTAINING AND CHLORINE-FREE HYDROCARBONS

This application is a continuation of application Ser. No. 07/759,793, filed on Sep. 13, 1991 now abandoned which is a continuation of application Ser. No. 651,846, filed Feb. 4, 1991, now abandoned.

The present invention relates to an improved process for the preparation of saturated, fluorine-containing and chlorine-free hydrocarbons.

It is known that 1,1,1,4,4,4-hexafluorobutane can be obtained by catalytic hydrogenation of 2-chloro- and/or 2,3-dichloro-1,1,1,4,4,4-hexafluorobutene at 50°±10° C. (see Huang Yaozeng et al., Youji Huoxue (2), p. 125 to 128 (1984), reported in C.A. 101, 54 548 u). The mixture present after the reaction in this case contains 56% of the desired 1,1,1,4,4,4-hexafluorobutane starting from the 2-chloro compound and only 18% starting from the 2,3-dichloro compound.

Saturated, fluorine-containing and chlorine-free hydrocarbons have recently been of particular industrial interest as insulating and blowing gases for synthetic foam materials and as a working liquid for heat pump systems which do not have a negative influence on the ozone layer of the earth's atmosphere (see, for example, DE-OS (German Published Specification) 3,735,467 and DE-OS (German Published Specification) 3,818,692).

In improved process for the preparation of saturated, fluorine-containing and chlorine-free hydrocarbons of the formula (I)

$$R_f\text{—}CH_2\text{—}CH_2\text{—}R_f \quad (I)$$

in which $R_f$ in each case represents $-(CF_2)_nCF_3$ with n=0 to 0 7, however both n taken together not more than 10 or both $R_f$ together represent

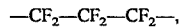

$$-CF_2-CF_2-CF_2-,$$

has now been found, by catalytically hydrogenating unsaturated, fluorine- and chlorine-containing hydrocarbons of the formula (II)

$$R_f\text{—}CX\text{=}CCl\text{—}R_f \quad (II)$$

in which,

X represents hydrogen or chlorine and $R_f$ has the meaning indicated in formula (I), which is characterized in that the hydrogenation is carried out in the gas phase at temperatures above 80° C.

In formulas (I) and (II) $R_f$ preferably represents $-(CF_2)_nCF_3$ with n=0 to 2.

The starting compounds of the formula (II) are 2-chloro-1,1,1,4,4,4-hexafluorobut-2-ene, 2,3-dichloro-1,1,1,4,4,4-hexafluorobut-2-ene, 1-chloro-3,3,4,4,5,5-hexafluorocyclopentene and 1,2-dichloro-3,3,4,4,5,5-hexafluorocyclopentene. These compounds are all known and easily accessible.

The catalytic hydrogenation can be carried out in a manner known per se, for example by passing a mixture of a compound of the formula (II) with hydrogen over a firmly attached hydrogenation catalyst. The molar ratio of the compound of the formula (II) to hydrogen can be, for example, 1:3 to 1:50. Preferably, it is 1:4 to 1:20.

The hydrogenation can be carried out, for example, at normal pressure or at elevated pressures, for example in the range from normal pressure to 20 bar. Preferably it is carried out at normal pressure.

Suitable hydrogenation catalysts are in particular those which contain transition metals on support materials. Of the transition metals, palladium and platinum are preferred, in particular palladium. Examples of support materials are carbon, for example in the form of carbon fibres, petroleum coke or active carbons, aluminas, silicas, barium sulphate, spinels, silicates and titanium dioxide. Active carbons and lithium-aluminium spinels are preferred. The catalysts can contain, for example, 0.5 to 50 g of transition metal per liter of support material. This content is preferably in the range 2 to 20 g/l.

The flow rate of the reaction mixture and the catalyst quantity can be chosen in such a way, for example, that catalyst weight hourly space velocities in the range from 20 to 2,000 g/l.h result. Weight hourly space velocities in the range from 50 to 800 g/l.h are preferred.

It is an essential feature of the present invention that the catalytic hydrogenation is carried out at temperatures above 80° C. Temperatures in the range 90° to 400° C. are preferred, in particular those from 95° to 250° C.

Surprisingly, saturated, fluorine-containing and chlorine-free hydrocarbons of the formula (I) according to the invention are obtained in distinctly better yields than in the known processes carried out at lower temperatures. In the process according to the invention, the conversions and the selectivities are in general above 80% in each case, and frequently the conversions are above 90%. This is particularly surprising, therefore, as the selectivity frequently decreases with increasing temperature and in the case of the substances to be employed according to the invention the risk of the elimination of hydrogen fluoride and thus the risk of the formation of less fluorinated products additionally exists at higher temperature.

The mixture present after the reaction according to the invention can be worked up, for example, by allowing the hydrogen chloride formed to escape as a gas and distilling the residue which remains at normal temperature. In order to obtain particularly pure products of the formula (I), the mixture present after the reaction can be washed, for example, with an aqueous-alkaline solution, then the organic phase can be removed and distilled over active carbon and magnesium.

EXAMPLES

Description of the apparatus used in carrying out the examples:

A vertical quartz tube which could be heated was packed with 200 ml of the catalyst indicated in each case and, after flushing with nitrogen, the charges indicated in each case were admitted at normal pressure. After 25 minutes, the gases leaving the quartz tube were examined by gas chromatography.

Example 1

Charges: 0.37 mol/h of $CF_3$—CH=CCl—$CF_3$, 2.5 mol/h of hydrogen.
Catalyst: palladium on Li—Al spinel (18 g/l).
Reaction conditions: 150° C., normal pressure.
Catalyst weight hourly space velocity: 360 g/l.h.
Conversion: 91%.
Selectivity for $CF_3$—$CH_2$—$CH_2$—$CF_3$: 78%.

Example 2

Charges: 0.66 mol/h of CF$_3$—CH=CCl—CF$_3$, mol/h of hydrogen.
Catalyst: As in Example 1.
Reaction conditions: 200° C., normal pressure.
Catalyst weight hourly space velocity: 650 g/l.h.
Conversion: 86%.
Selectivity for CF$_3$—CH$_2$—CH$_2$—CF$_3$: 81%.

Example 3

Charges: 0.41 mol/h of CF$_3$—CH=CCl—CF$_3$, 2.5 mol/h of hydrogen.
Catalyst: palladium on active carbon (5 g/l).
Reaction conditions: 100° C., normal pressure.
Catalyst weight hourly space velocity: 410 g/l.h.
Conversion: 100%.
Selectivity for CF$_3$—CH$_2$—CH$_2$—CF$_3$: 100%.

Example 4

Charges: 0.33 mol/h of CF$_3$—CH=CCl—CF$_3$, 2 mol/h of hydrogen.
Catalyst: As in Example 3.
Reaction conditions: 200° C., normal pressure.
Catalyst weight hourly space velocity: 320 g/l.h.
Conversion: 89%.
Selectivity for CF$_3$—CH$_2$—CH$_2$—CF$_3$: 91%.

Example 5

Charges: 0.41 mol/h of CF$_3$—CH=CCl—CF$_3$, 2.5 mol/h of hydrogen.
Catalyst: palladium on Li—Al spinel (5 g/l).
Reaction conditions: 100° C., normal pressure.
Catalyst weight hourly space velocity: 410 g/l.h.
Conversion: 82%.
Selectivity for CF$_3$—CH$_2$—CH$_2$—CF$_3$: 83%.

Example 6

Charges: 0.37 mol/h of CF$_3$—CCl=CCl—CF$_3$, 3.7 mol/h of hydrogen.
Catalyst: palladium on Li—Al spinel (18 g/l).
Reaction conditions: 150° C., normal pressure.
Catalyst weight hourly space velocity: 440 g/l.h.
Conversion: 98%.
Selectivity for CF$_3$—CH$_2$—CH$_2$—CF$_3$: 81.5%.

Example 7

Carrying-out as in Example 6, but at 200° C.
Conversion: 93.9%.
Selectivity for CF$_3$—CH$_2$—CH$_2$—CF$_3$: 84.3%.

Example 8

Charges: 0.17 mol/h of CF$_3$—CH=CCl—CF$_3$, 2.5 mol/h of hydrogen.
Catalyst: As in Example 6.
Reaction conditions: 200° C., normal pressure.
Catalyst weight hourly space velocity: 200 g/l.h.
Conversion: 99.5%.
Selectivity for CF$_3$—CH$_2$—CH$_2$—CF$_3$: 93.3%.

Example 9

Charges: 0.17 mol/h of 1,2-dichlorohexafluorocyclopentene, 2.5 mol/h of hydrogen.
Catalyst: palladium on Li—Al spinel (18 g/l).
Reaction conditions: 200° C., normal pressure.
Catalyst weight hourly space velocity: 210 g/l.h.
Conversion: 98.5%.
Selectivity for 1,1,2,2,3,3-hexafluorocyclopentane: 98%.

Example 10

Charges: 6.3 mol of 1,2-dichlorohexafluorocyclopentene, 45 mol of hydrogen in the course of 7.7 hours.
Catalyst: As in Example 9.
Reaction conditions: 200° C., normal pressure.
Catalyst weight hourly space velocity: 200 g/l.h.
Yield: 1,035 g
Selectivity for 1,1,2,2,3,3-hexafluorocyclopentane: 97%.

What is claimed is:

1. A process for the preparation of $$1,1,1,4,4,4\text{-hexafluorobutane} \qquad (I)$$

by catalytically hydrogenating unsaturated, fluorine- and chlorine-containing hydrocarbons of the formula $$CF_3—CX=CCl—CF_3 \qquad (II)$$

in which
X represents hydrogen or chlorine
in which process the hydrogenation is carried out in the gas phase at temperatures above 80° C. without the presence of a base, and in the presence of a catalyst selected from the group consisting of palladium on active carbon and palladium on LiAl-spinel, and wherein the reaction product produced by said process is worked up by allowing hydrogen chloride formed during the process to escape as a gas, and distilling the residue which remains to remove any unreacted starting materials and any remaining HCl to obtain a product which is chlorine free.

2. The process of claim 1, in which the molar ratio of the compound of the formula (II) to hydrogen is 1:3 to 1:50.

3. The process of claim 1, which is carried out at a pressure in the range from normal pressure up to 20 bar.

4. The process of claim 1, in which the flow rate of the reaction mixture and the catalyst quantity are chosen such that catalyst weight hourly space velocities in the range from 20 to 2,000 g/l.h result.

5. The process of claim 1, which is carried out at a temperature in the range 90° to 400° C.

6. The process of claim 1, which is carried out at temperatures in the range from 95° to 250° C.

* * * * *